United States Patent
Deane et al.

(10) Patent No.: US 11,571,131 B2
(45) Date of Patent: Feb. 7, 2023

(54) METHOD AND SYSTEM FOR IMPROVED MEASUREMENT OF LOCALIZED ORAL INFLAMMATION USING MODULATED LIGHT

(71) Applicant: KONINKLIJKE PHILIPS N.V., Eindhoven (NL)

(72) Inventors: Steven Charles Deane, Cambridge (GB); Alan James Davie, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 294 days.

(21) Appl. No.: 16/770,878

(22) PCT Filed: Dec. 5, 2018

(86) PCT No.: PCT/EP2018/083589
§ 371 (c)(1),
(2) Date: Jun. 8, 2020

(87) PCT Pub. No.: WO2019/115307
PCT Pub. Date: Jun. 20, 2019

(65) Prior Publication Data
US 2021/0161392 A1   Jun. 3, 2021

Related U.S. Application Data

(60) Provisional application No. 62/597,635, filed on Dec. 12, 2017.

(51) Int. Cl.
*A61B 5/00* (2006.01)
*A61B 5/1455* (2006.01)

(52) U.S. Cl.
CPC ........ *A61B 5/0088* (2013.01); *A61B 5/14552* (2013.01); *A61B 5/4552* (2013.01);
(Continued)

(58) Field of Classification Search
CPC ... A61B 5/0088; A61B 5/7228; A61B 5/7282; A61B 5/1455; A61B 5/14551;
(Continued)

(56) References Cited

U.S. PATENT DOCUMENTS 7,440,788 B2   10/2008   Jenkins et al.
9,517,015 B2   12/2016   Deane et al.
(Continued)

FOREIGN PATENT DOCUMENTS

EP     3213683 A1    9/2017
WO   2009153700 A1  12/2009
(Continued)

OTHER PUBLICATIONS

International Search Report and Written Opinion, International Application No. PCT/EP2018/083589, dated Mar. 25, 2019.

*Primary Examiner* — Chu Chuan Liu (57) ABSTRACT

A method for localizing gingival inflammation using an oral care device, comprising: (i) simultaneously emitting (520) light by a plurality of light sources (48) of the oral care device, wherein at least some of the plurality of light sources emit light of different wavelengths to result in a plurality of emitted light wavelengths, wherein each of the different wavelengths is modulated with a distinct code; (ii) obtaining (530), by a light detector (40) of the oral care device, reflectance measurements from a location within the user's mouth to generate reflectance data for the location; (iii) demodulating (540), by a controller (30) of the oral care device, the obtained reflectance data; and (iv) determining (560), by the controller using the demodulated reflectance data, whether gingiva at the location is inflamed.

17 Claims, 6 Drawing Sheets

(52) U.S. Cl.
CPC .......... *A61B 5/7228* (2013.01); *A61B 5/7282* (2013.01); *A61B 2562/0233* (2013.01); *A61B 2562/04* (2013.01); *A61B 2576/02* (2013.01)

(58) Field of Classification Search
CPC ............ A61B 5/14552; A61B 5/14532; A61B 5/4552; A61B 5/0075; A61B 5/7405; A61B 5/742; A61B 5/7207; A61B 5/746; A61B 5/7455; A61B 5/0059; A61B 2546/02

See application file for complete search history.

(56) References Cited

U.S. PATENT DOCUMENTS

| | | |
|---|---|---|
| 9,526,598 B2 | 12/2016 | Van Gool et al. |
| 2005/0187451 A1* | 8/2005 | Norris ................ A61B 5/14551 600/326 |
| 2006/0135869 A1 | 6/2006 | Farina |
| 2011/0092824 A1* | 4/2011 | Veen ................. A61B 5/14551 600/477 |
| 2016/0270716 A1* | 9/2016 | Guan ................. A61B 5/7264 |

FOREIGN PATENT DOCUMENTS

| | | |
|---|---|---|
| WO | 2015069704 A1 | 5/2015 |
| WO | 2017125926 A2 | 7/2017 |

* cited by examiner

METHOD AND SYSTEM FOR IMPROVED MEASUREMENT OF LOCALIZED ORAL INFLAMMATION USING MODULATED LIGHT

This application is the U.S. National Phase application under 35 U.S.C. § 371 of International Application No. PCT/EP2018/083589, filed on 20 Jun. 2019, which claims the benefit of U.S. Provisional Application No. 62/597,635, filed 12 Dec. 2017. These applications are hereby incorporated by reference herein.

FIELD OF THE INVENTION

The present disclosure is directed generally to methods and systems for improved detection of localized gingival inflammation using an oral care device.

BACKGROUND

Proper tooth brushing, including length and coverage of brushing, helps promote long-term dental health. Many dental problems are experienced by individuals who either do not regularly brush their teeth or who do so inadequately, especially in a particular area or region of the oral cavity. Among individuals who do brush regularly, improper brushing habits can result in poor coverage of brushing and thus surfaces that are not adequately cleaned during a cleaning session, even when a standard brushing regimen, such as brushing for two minutes twice daily, is followed.

Indeed, it is estimated that 50% of the adult population in the United States is affected by periodontal disease, with severity of disease ranging from gingivitis to periodontitis. However, consumers are often not able to detect early signs of periodontal disease. Accordingly, such diseases may only be detected during dental visits when the disease is already advanced and significantly harder to treat.

Inflammation of tissues within the mouth is one of the key signs of periodontal disease. Detecting inflammation would signal the existence of a disease state, and would alert the individual to the need for treatment to address the issue. For example, inflammation of the gums can be reversible with proper home care if it is detected, while bone loss from periodontitis will require professional treatment. However, existing methods and devices are unable to adequately identify or quantify inflammation of tissues, particularly localized inflammation. For example, handheld devices enable poor detection of gingival inflammation, as these devices either analyze large areas of the mouth resulting in a large signal-to-noise ratio that interferes with detection, or require so many measurements that they are not user friendly. Additionally, the motion of a user's hand can result in artifacts and poor readings by a handheld device. As a result, periodontal disease is often not detected.

Accordingly, there is a continued need in the art for oral care methods and devices that account for the motion of a user's hand during the detection of localized gingival inflammation.

SUMMARY OF THE INVENTION

The present disclosure is directed to inventive methods and systems for detecting tissue inflammation using an oral care device. Various embodiments and implementations herein are directed to an oral care device configured to obtain measurements of gingival tissue to identify localized gingival inflammation. The oral care device comprises a sensor with a configuration of one or more light emitters and one or more photodetectors or imagers to obtain information about gingival tissue at one or more sampled locations. The one or more light emitters are configured to emit light such that a plurality of different wavelengths are simultaneously emitted. Each of the different wavelengths is modulated with a distinct code such that a light detector can simultaneously detect and identify the different wavelengths. The one or more light detectors obtain reflectance measurements from a location within the user's mouth to generate reflectance data for the location, and a processor demodulates the obtained reflectance data. The oral care device then determines whether gingiva at that location is inflamed.

Generally in one aspect, a method for localizing gingival inflammation within a user's mouth using an oral care device is provided. The method includes: (i) simultaneously emitting light by a plurality of light sources of the oral care device, wherein at least some of the plurality of light sources emit light of different wavelengths to result in a plurality of emitted light wavelengths, wherein each of the different wavelengths is modulated with a distinct code; (ii) obtaining, by a light detector of the oral care device, reflectance measurements from a location within the user's mouth to generate reflectance data for the location; (iii) demodulating, by a controller of the oral care device, the obtained reflectance data; and (iv) determining, by the controller using the demodulated reflectance data, whether gingiva at the location is inflamed.

According to an embodiment, the method further includes the step of determining, by the controller using demodulated reflectance data, whether the location comprises gingiva.

According to an embodiment, the method further includes the step of providing information regarding whether gingiva at a location comprises inflammation.

According to an embodiment, the step of determining whether gingiva at a location is inflamed comprises determining an approximate tissue oxygenation level of the gingiva at each of the remaining plurality of locations, wherein a low tissue oxygenation level indicates gingiva inflammation.

According to an embodiment, the oral care device comprises a plurality of light detectors, each configured to obtain reflectance measurements from a different location within the user's mouth to generate reflectance data for that respective location. According to an embodiment, each of the plurality of light detectors obtain reflectance measurements simultaneously. According to an embodiment, the plurality of light detectors obtain reflectance measurements sequentially.

According to an embodiment, the plurality of light sources and the light detector are positioned such that a surface at the location is not directly illuminated by the plurality of light sources.

According to an aspect is a method for localizing gingival inflammation using an oral care device. The method includes: (i) emitting light by a plurality of light sources of the oral care device, wherein at least some of the plurality of light sources are each configured to emit light modulated with a distinct code; (ii) obtaining, by a light detector of the oral care device, reflectance measurements from a location within the user's mouth to generate reflectance data for the location; (iii) demodulating, by a controller of the oral care device, the obtained reflectance data; and (iv) determining, by the controller using the demodulated reflectance data, whether gingiva at the location is inflamed.

According to an aspect is a device configured to localize gingival inflammation within a user's mouth. The device includes: a plurality of light sources configured to emit light, wherein at least some of the plurality of light sources emit light of different wavelengths to result in a plurality of emitted light wavelengths, wherein each of the different wavelengths is modulated with a distinct code; a light detector configured to obtain reflectance measurements from a location within the user's mouth to generate reflectance data for the location; and a controller configured to: (i) demodulate the obtained reflectance data; and (ii) determine, using the demodulated reflectance data, whether gingiva at the location is inflamed.

According to an embodiment, the controller is further configured to determine, from the demodulated reflectance data, whether the location comprises gingiva.

According to an embodiment, the device further includes a user interface configured to provide information regarding whether gingiva at a location comprises inflammation.

As used herein for purposes of the present disclosure, the term "controller" is used generally to describe various apparatus relating to the operation of an oral care apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a method and device for detecting gingival inflammation using an oral care device. More generally, Applicant has recognized and appreciated that it would be beneficial to provide a system to detect localized tissue inflammation. Accordingly, the methods described or otherwise envisioned herein provide a device such as an oral care device configured to obtain measurements of gingival tissue. The oral care device comprises one or more of a variety of sensor arrays having at least one light emitter and at least one light detector to obtain information about gingival tissue at one or more sampled locations. The light sources of the one or more light emitters are configured to emit light such that a plurality of different wavelengths are simultaneously emitted by the plurality of light sources. Each of the different wavelengths is modulated with a distinct code such that a light detector can simultaneously detect and identify the different wavelengths. The one or more light detectors obtain reflectance measurements from a location within the user's mouth to generate reflectance data for the location, and a processor demodulates the obtained reflectance data. The device uses the demodulated data to determine whether gingiva at that location is inflamed. The oral care device can then report that information to the user or a third party.

The embodiments and implementations disclosed or otherwise envisioned herein can be utilized with any oral device, including but not limited to a toothbrush, a flossing device, an oral irrigator, or any other oral device. For example, one application of the embodiments and implementations herein is to assess inflammation of gingival tissues using a specialized handheld oral inflammation detection device. Another application is to assess inflammation of gingival tissues using an oral care. However, the disclosure is not limited to a device such as described herein, and thus the disclosure and embodiments disclosed herein can encompass any oral device.

Figure 1:
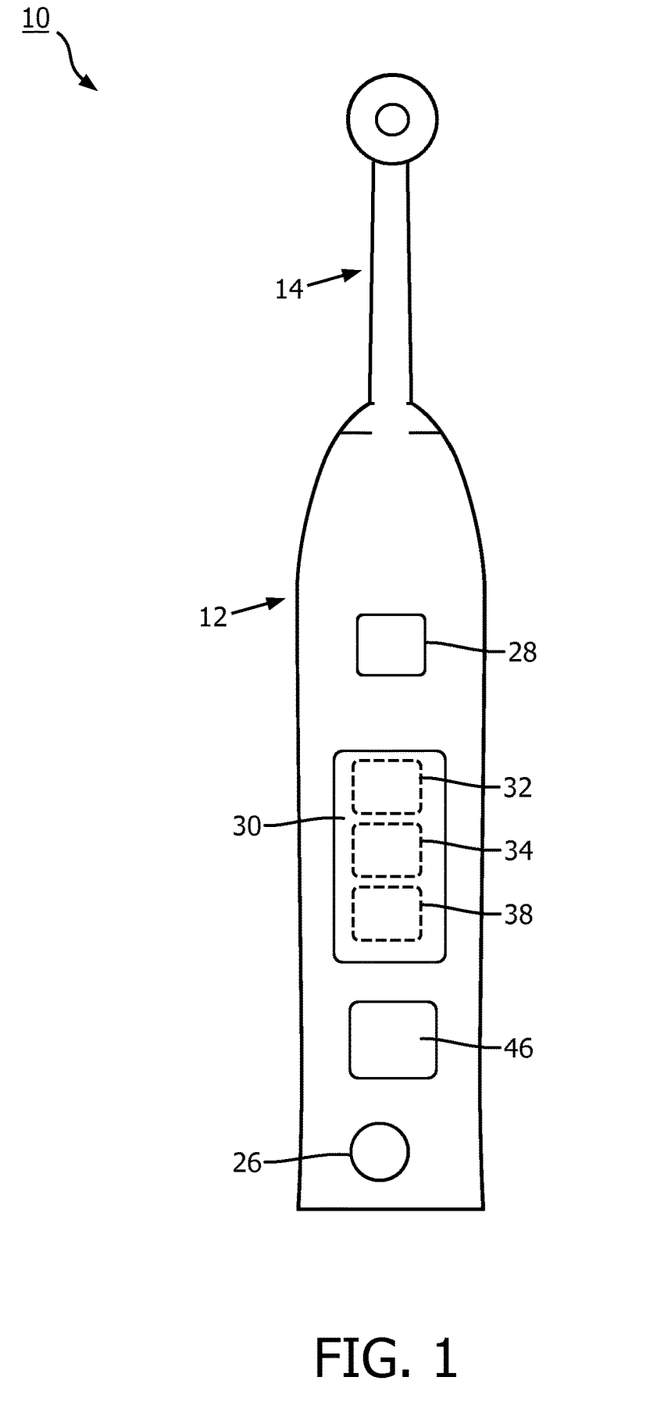
FIG. 1 is a schematic representation of an oral care device, in accordance with an embodiment.

Referring to FIG. 1, in one embodiment, is an oral care device 10 with a body portion 12 and a nozzle member 14 mounted on the body portion. According to an embodiment, nozzle member 14 may be configured to allow the passage of pressurized liquid and/or air from a reservoir in the body 12 (not shown) to the nozzle head where it is applied to the user's interdental regions. Nozzle member 14 can be detachably mounted onto body portion 12 such that the nozzle can periodically be replaced with a new one when a component of the device is worn out or otherwise requires replacement.

Body portion 12 is further provided with a user input 26. The user input 26 allows a user to operate the oral care device 10, for example to turn the oral care device on and off. The user input 26 may, for example, be a button, touch screen, or switch.

Oral care device 10 optionally includes one or more sensors 28. Sensor 28 is shown in FIG. 1 within body portion 12, but may be located anywhere within the device. Sensor 28 may be used to characterize the orientation and displacement of the device. According to an embodiment, these sensors provide information about the position of the device with respect to a user's body part, a fixed point, and/or one or more other positions. According to an embodiment, sensor 28 is disposed in a predefined position and orientation in the oral cleaning device 10, and the nozzle is in a fixed spatial relative arrangement to sensor 28. Therefore, the orientation and position of the nozzle can be easily determined based on the known orientation and position of the sensor 28.

The information generated by the first sensor 28 is provided to a controller 30. Controller 30 may be formed of one or multiple modules, and is configured to operate the oral cleaning device 10 in response to an input, such as input obtained via user input 26. According to an embodiment, the sensor 28 is integral to the controller 30. Controller 30 can comprise, for example, at least a processor 32, a memory 34, and a connectivity module 38. The processor 32 may take any suitable form, including but not limited to a microcontroller, multiple microcontrollers, circuitry, a single processor, or plural processors. The memory 34 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of oral cleaning device 10. According to an embodiment, connectivity module 38 transmits collected sensor data, and can be any module, device, or means capable of transmitting a wired or wireless signal, including but not limited to a Wi-Fi, Bluetooth, near field communication, and/or cellular module.

According to an embodiment, oral care device 10 includes a user interface 46 configured to provide information to a user before, during, and/or after a care session. The user interface 46 can take many different forms, but is configured to provide information to a user. For example, the information can be read, viewed, heard, felt, and/or otherwise interpreted concerning inflammation of one or more tissues within the mouth. According to an embodiment, the user interface 46 provides feedback to the user that includes information about where tissues are inflamed, and/or how much inflammation is present. Accordingly, the user interface may be a display that provides information to the user, a haptic mechanism that provides haptic feedback to the user, a speaker to provide sounds or words to the user, or any of a variety of other user interface mechanisms. For example, the system may provide feedback via a smartphone app, a website, or via any other interface configured to share information with the user.

Figure 2:
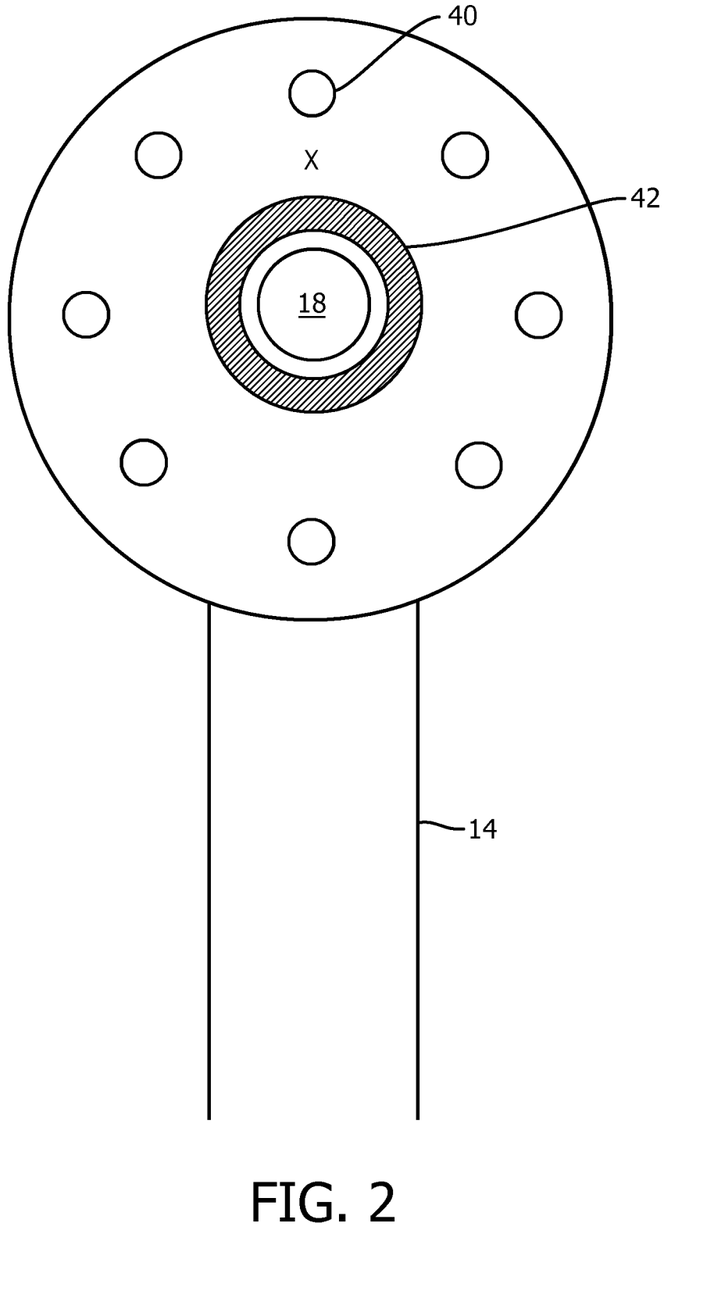
FIG. 2 is a schematic representation of a head of an oral care device, in accordance with an embodiment.

Referring to FIG. 2, in one embodiment, is a nozzle 14 of an oral care device. The nozzle includes a nozzle portion, with a centrally-located guidance tip 18. According to one embodiment, the nozzle head comprises at least one light emitter 42 and at least one light receiver 40. According to the embodiment depicted in FIG. 2, the light emitter 42 is a ring-shaped bundle of light-emitting fibers or a light-emitting light guide, although it can be many other shapes and sizes. The one or more light emitters can be or comprise any light source, such as an LED light source, that emits light capable of facilitating the detection of gingival inflammation. According to an embodiment, the one or more light emitters comprise light from one or more light sources 48 such as LEDs, and are connected by a light fiber or light guide from the LEDs to the light emitter on the surface of the oral care device. According to an embodiment the light source generates light in at least two wavelengths, such as 480 nm and 680 nm that allows for the characterization of oxygen saturation in human tissue, and hence the detection of localized inflammation. Generally, tissue exhibiting low tissue oxygenation indicates gingival inflammation.

Similarly, the one or more light receivers 40 are any light receivers capable of facilitating the detection of gingival inflammation. For example, according to an embodiment the light receivers are a photodetector or photodiode, or any other sensor capable of detecting light emitted by the light emitter 42. According to an embodiment, the light receivers are photodiodes connected to light fibers or light guides. Each light receiver may be configured to detect two or more wavelengths, or alternatively each light receiver may be configured to detect only a single wavelength. According to another embodiment, light receiver 40 is a pixel array configured to obtain one or more images of the tissue illuminated by the light emitted from the light emitter 42. The light receiver may comprise a plurality of detection fibers that are used simultaneously or may be time-multiplexed.

One advantage of the design of the oral care device in FIG. 2 is that the sensors are able to capture spatial information as well as gingival inflammation information. Since the information associated with each emitter-receiver couple comes from a unique tissue location, the localization of the inflammation is known.

In this embodiment, the guidance tip 18 provides a tactile feedback to the user, which facilitates proper interdental positioning near the gums. According to an embodiment, when properly positioned in the mouth, each light receiver 40 measures a different part of the tissue surface, which is approximately the location between the light emitter and the light receiver. For example, when placed on the junction between two teeth and the gingiva the light emitter will illuminate the whole area, and several light receivers 40 will be on the gingiva to detect inflammation, while others will be simultaneously placed on the teeth which can be easily distinguished from the measured spectral response.

Figure 3:
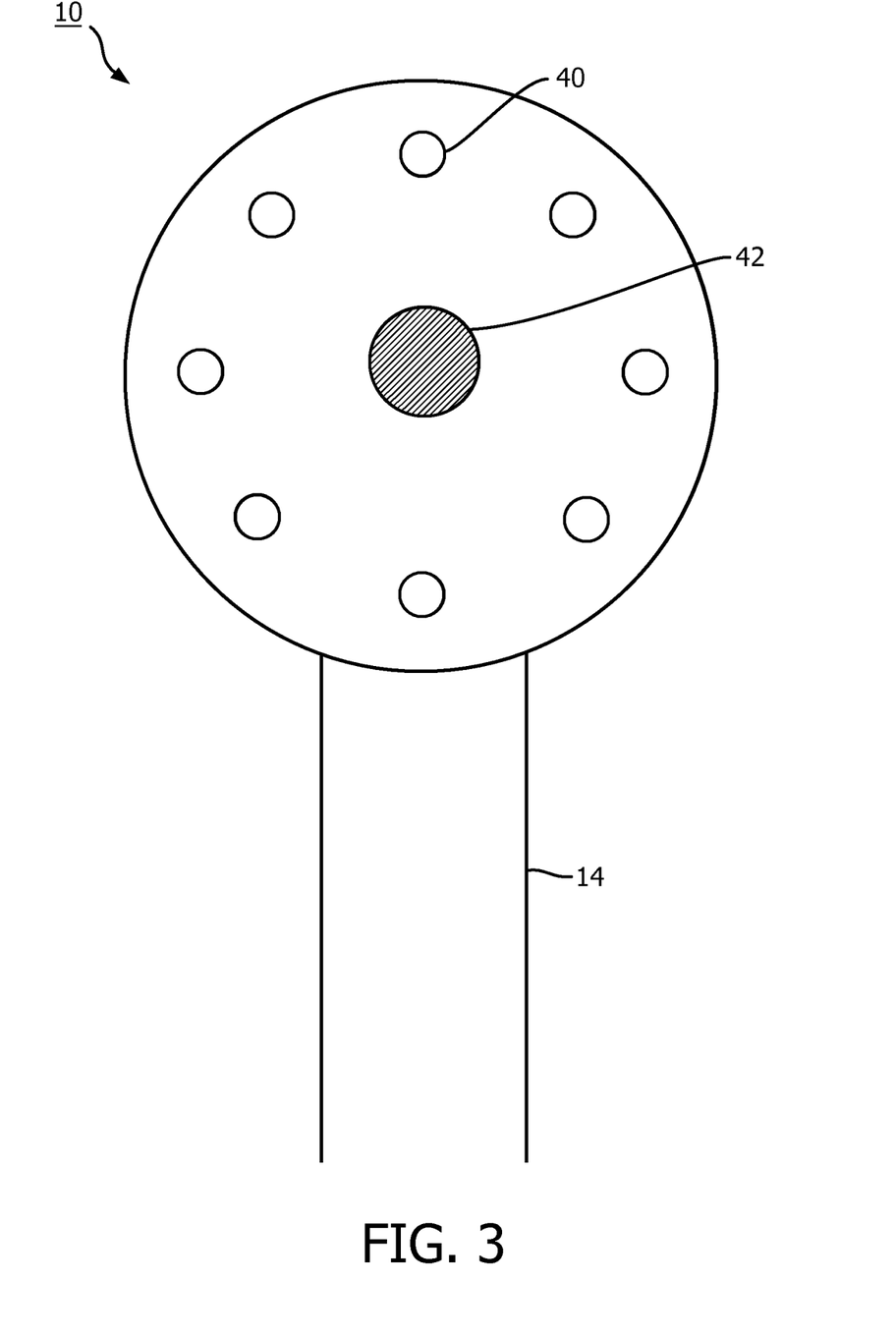
FIG. 3 is a schematic representation of a head of an oral care device, in accordance with an embodiment.

According to an embodiment, many different configurations of light emitters 42 and light detectors 40 are possible. Referring to FIG. 3, for example, is an embodiment of an oral care device 10 configured primarily to measure gingival inflammation. The oral care device comprises a head portion having a single centralized light emitter 42 and a plurality of light detectors 40. According to a similar embodiment, the device may comprise a single centralized light detector 40 and one or more light emitters 42.

The one or more light emitters 42 and light detectors 40 are positioned on device 10 such that the surfaces of the gingival tissue from which data is obtained are not directly illuminated by the light emitter. For example, referring to FIG. 2, the light emitter 42 emits light into the tissue in front of it, and light detector 40 obtains reflectance data from the tissue located at or very near the "X" shown on the device, although the light detector could also obtain reflectance data from the tissue located in front of it as well. According to an embodiment, therefore, the light emitters and the surfaces from which data is obtained are not overlapping. This is in contrast to a camera system in which imaged surfaces are directly illuminated. When a surface is directly illuminated, for example, detection or an image is dominated by near-surface scattering, which prevents the analysis of the gingival tissue as described herein.

Figure 4:
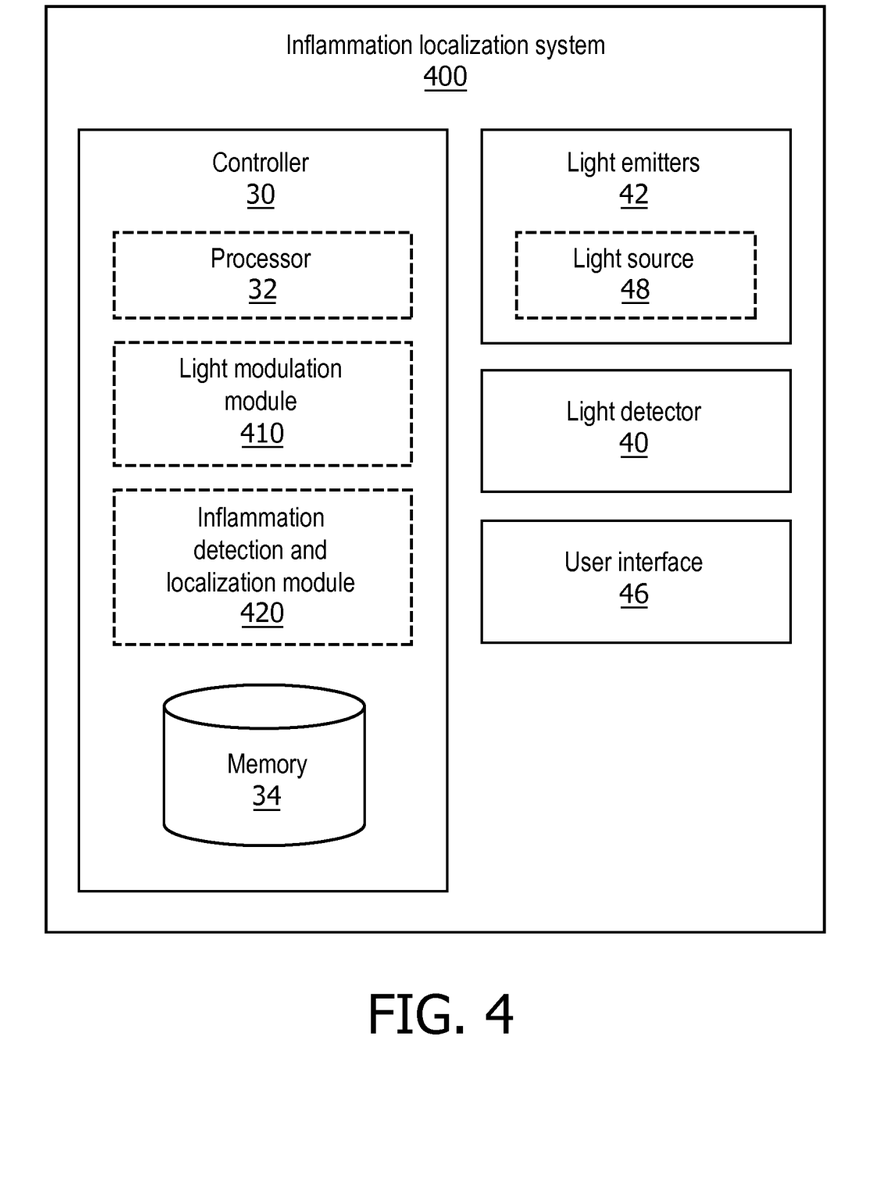
FIG. 4 is a schematic representation of an inflammation localization system, in accordance with an embodiment.

Referring to FIG. 4, in one embodiment, is an inflammation localization system 400. According to an embodiment, inflammation localization system 400 includes a controller 30 comprising a processor 32 and a memory 34. The inflammation localization system also comprises one or more light emitters 42 each with one or more light sources 48. Inflammation localization system 400 includes one or more light detectors 40 which provide sensor data to the controller 30. Controller 30 of inflammation localization system 400 includes a light modulation module 410. The light modulation module 410 modulates the light emitted by the one or more light emitters 42, as described or otherwise envisioned herein. The light modulation module 410 also demodulates the light detected by the one or more light detectors 40.

Controller 30 of inflammation localization system 400 includes an inflammation detection and localization module 420. The inflammation detection and localization module analyzes demodulated sensor data from the one or more light detectors 40, received from the light modulation module 410, and determines whether the analyzed tissue is inflamed and where that tissue is located. The inflammation detection and localization module may also optionally include device localization information from sensor 28.

According to an embodiment, inflammation localization system 400 includes a user interface 46 which provides information to the user about the status and/or location of the tissue. User interface 46 can be or can comprise a feedback module that provides direct feedback to the user via a haptic signal, audio signal, visual signal, and/or any other type of signal.

According to an embodiment, inflammation localization system 400 can be implemented in any device configured to come into proximity with tissues that can be quantified. For example, inflammation localization system 400 can be implemented as another oral care device such as a toothbrush, an oral irrigator, a tongue cleaner, or any other oral care device.

Figure 5:
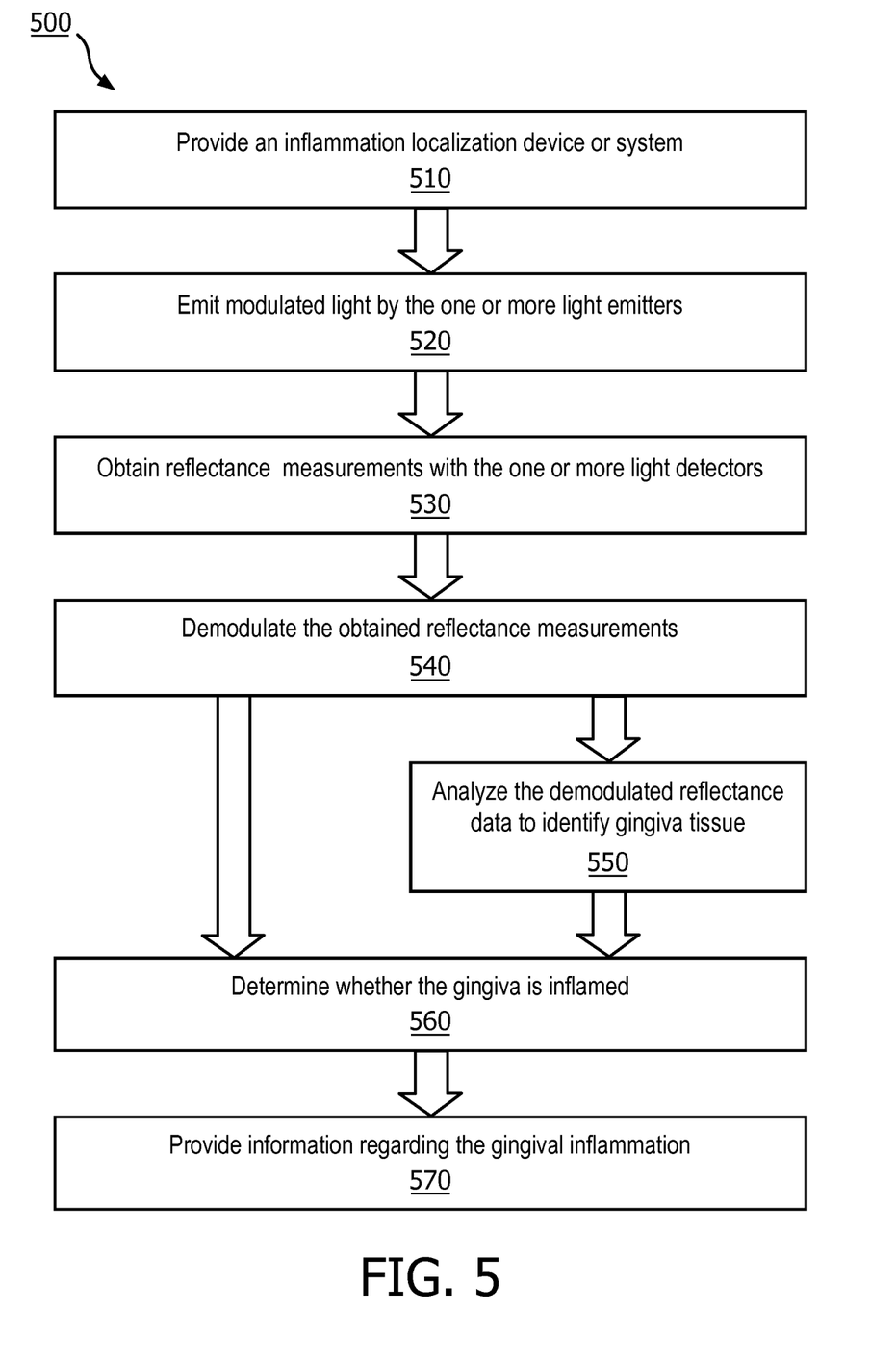
FIG. 5 is a flowchart of a method for localizing gingiva inflammation, in accordance with an embodiment.

Referring to FIG. 5, in one embodiment, is a flowchart of a method 500 for localizing inflammation of gingival tissue within a user's mouth. In step 510, an inflammation localization system is provided. The inflammation localization system may be any of the devices or systems described or otherwise envisioned herein. Generally, the inflammation localization system will comprise one or more light emitters 42 with one or more light sources 48, one or more light detectors 40, a light modulation module 410 configured to modulate the light emitted by the one or more light emitters and to demodulate the light detected by the one or more light detectors, and an inflammation detection and localization module 420 configured to analyze the demodulated data to identify inflamed gingiva. Many other components and configurations are possible. Although method 500 is described within the framework of an oral care device 10, the method can be implemented using any other inflammation localization analysis system.

At step 520 of the method, the one or more light emitters 42 emit light, a beam of each of which impacts the gingival tissue. According to an embodiment, the emitted light only indirectly impacts the gingival tissue that is analyzed by the light detector 40. A light emitter may comprise one or more light sources 48, and the system may be configured to activate the one or more light emitters in response to a trigger. The light emitters may be spaced apart or co-located, depending on the design of the device.

At least some of the one or more light emitters are configured such that different wavelengths of light are emitted. For example, the device may be configured such that different wavelengths are emitted by different light emitters, and/or the device may be configured such that different wavelengths are emitted by different light sources 48 of a light emitter 42. As a result, the device comprises a plurality of emitted light wavelengths. According to an embodiment, for effective gingivitis detection, several wavelengths must be sampled at each location to give a measured spectrum from which tissue oxygenation can be measured and gingival condition can be assessed. For example, high oxygenation indicated gum health while low oxygenation indicated gingivitis. The number of wavelengths can be as low as two, or it can be a detailed spectrum with hundreds of channels, although for most purposes the number of wavelengths is between four and eight.

The light emitted by the one or more light emitters is modulated with a distinct code, such as an orthogonal code, such that the one or more light emitters can simultaneously emit light at different frequencies, each with a unique code, and the light detector can obtain reflectance measurements and demodulate the data to identify specific frequencies of emitted light from the data. According to an embodiment, light modulation module 410 is configured to modulate the light emitted by the one or more light emitters.

Figure 6:
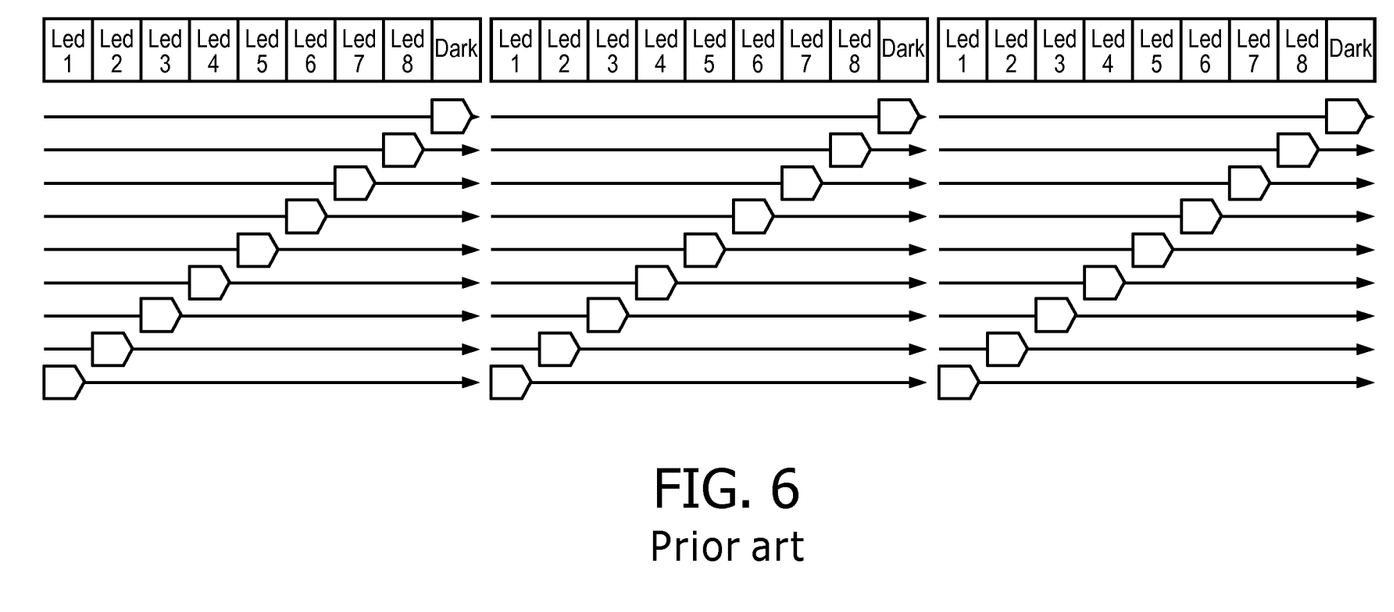
FIG. 6 is a flowchart of a prior art method for emitting light by a plurality of LEDs.

Prior art devices use time-division multiple access (TDMA) to obtain sensor data by a light detector for a plurality of wavelengths. For example, according to this prior art method the one or more light sources emit light of different wavelengths sequentially. Referring to FIG. 6 is a schematic representation of a prior art TDMA method for obtaining data for a plurality of wavelengths. The system may comprise a plurality of LEDs each emitting light comprising a different wavelength, and further comprises a light detector. Each LED emits light in a sequence, and is detected by the light detector. A dark period of no emitted light may be utilized for background illuminance purposes. Motion between the sampling events skews the data and produces noise in the resulting readings.

In contrast, modulated light enables the simultaneous measurement by the light detector of emitted light of different wavelengths. According to an embodiment, oral care device 10 modulates all wavelengths simultaneously, each with a different code, thereby spreading all measurements over all time points. The device may modulate emitted light using any light modulation method. For example, the light may be modulated by adjusting the amplitude of the light, the phase of the light, and/or the on/off state of the light, among many other possible modulations.

According to an embodiment, the codes utilized to modulate the emitted light may be any possible code. There are many possible codes and code generation methods, such as Barker codes, Walsh codes, and so on, that can create a family of codes with low-zero correlation properties between different codes. Walsh codes, for example, are orthogonal codes with no DC content in the cross-correlation result, which can easily be constructed for a number of codes given by a power of two by the following equations:

$$W_1 = [0] \qquad \text{(Eq. 1)}$$

-continued $$W_{2n} = \begin{bmatrix} W_n & W_n \\ W_n & \overline{W_n} \end{bmatrix} \quad \text{(Eq. 1)}$$

This results in the following sets of codes for an embodiment in which there are two, four, or eight codes:

$$W_2 = \begin{bmatrix} 0 & 0 \\ 0 & 1 \end{bmatrix}$$

$$W_4 = \begin{bmatrix} 0 & 0 & 0 & 0 \\ 0 & 1 & 0 & 1 \\ 0 & 0 & 1 & 1 \\ 0 & 1 & 1 & 0 \end{bmatrix}$$

$$W_8 = \begin{bmatrix} 0 & 0 & 0 & 0 & 0 & 0 & 0 & 0 \\ 0 & 1 & 0 & 1 & 0 & 1 & 0 & 1 \\ 0 & 0 & 1 & 1 & 0 & 0 & 1 & 1 \\ 0 & 1 & 1 & 0 & 0 & 1 & 1 & 0 \\ 0 & 0 & 0 & 0 & 1 & 1 & 1 & 1 \\ 0 & 1 & 0 & 1 & 1 & 0 & 1 & 0 \\ 0 & 0 & 1 & 1 & 1 & 1 & 0 & 0 \\ 0 & 1 & 1 & 0 & 1 & 0 & 0 & 1 \end{bmatrix}$$

Each channel can be a narrow band light source such as an LED, and can be modulated by a code provided by one row of these matrices. All wavelengths are detected simultaneously by the broadband light detectors, and digital filtering in the microcontroller can recover the separate channels by cross-correlation with the known codes. It is not necessary that all codes be used, so there will be a set of codes, such as Walsh codes, larger than the number of wavelengths to be detected.

According to another embodiment, the oral care device can sample multiple physical locations at once and must measure the spectrum at each location. This may be necessary, for example, to cope with the variety of ways the user can position the device, and the varying oral geometry between locations. According to this embodiment, the device may sample the full spectrum for each location sequentially to minimize motion during spectral measurement. Motion between each full-spectrum location measurement does not lead to errors in measuring tissue oxygenation, in contrast to measuring multiple channels sequentially at one location. Accordingly, each light detector can be rapidly sampled in turn, and each color channel per location be recovered by the correlation process inside the microcontroller, as described herein.

According to another embodiment, both the light emitters and the light detectors can be modulated using a suitable division of the codes such that all color channels at each light detector location are being measured simultaneously. For example, the codes for light emitters and light detectors can both be Walsh codes running at different rates, as can be seen from the reclusive definition of the Walsh codes. In effect, one coding scheme is nested inside the other coding scheme, but the complete orthogonality between different color channel and physical locations can be maintained.

According to an embodiment, signal modulation provides significantly improved motion robustness and reduces noise levels, as only noise that correlates with the chosen code is detected in the receiver. This can improve the signal-to-noise ratio by the square root of the code length, resulting in significant improvements. For this reason, a longer code than strictly needed may be utilized in some embodiments.

At step 530 of the method, at least one light detector 40 obtains reflectance data, such as reflectance from the surfaces reflecting light emitted by the one or more light emitters 42. The light detector may obtain data continuously or may only obtain data in response to a trigger. For example, the light detector may be triggered to obtain sensor data in response to activation of a light emitter.

As discussed herein, a light detector 40 may be positioned in a non-overlapping position relative to a light emitter 42 such that the detected tissue is only indirectly illuminated by the light from the light emitter. This configuration of the light detector(s) and the light emitter(s) results in a significant improvement in both the device and detection of inflammation. For example, the non-overlapping configuration described or otherwise envisioned herein maximizes the signal-to-noise ratio and enhances detection of localized gingival inflammation, among other benefits, by reducing near-surface scattering and other inhibitory factors. The one or more light detectors 40 of the oral care device can be positioned in any position in or on the oral care device, and may be positioned to obtain information about a variety of locations of the mouth or other surface being analyzed.

According to an embodiment, the one or more light detectors 40 are broadband detectors configured to obtain broadband spectral data. The light detectors will be configured to obtain, at a minimum, data for the wavelengths necessary to evaluate the oxygenation of the gingiva, to distinguish between gingiva and non-gingiva tissue, and/or other parameters necessary to perform care using the device. Accordingly, the one or more light emitters 42 can be configured to emit coded light using a single light source 48 such as a white LED, and the receiving light detector 40 and/or controller will split the received light into several wavebands for detection.

Once the one or more light detectors 40 obtains reflectance data, that data can be communicated continuously or periodically to the controller. Optionally, the obtained reflectance data can be stored in a temporary or long-term memory for analysis at a later time.

At step 540 of the method, the controller 30 of oral care device 10 has received the reflectance data obtained by the one or more light detectors 40 and demodulates the modulated data. For example, data may be demodulated using the light modulation module 410 of system 400. The data may be demodulated using any method for signal demodulation.

At optional step 550 of the method, controller 30 of oral care device 10 analyzes the demodulated reflectance data to determine which of the plurality of analyzed locations are and/or are not gingiva. According to one embodiment, the inflammation detection and localization module 420, which can be implemented as an algorithm, analyzes the demodulated reflectance data in one or more steps. For example, as an initial step, the module rejects potential outliers in the data. Outliers may include spurious measurements, as well as reflectance data from objects that are likely not gingival tissues, such as food debris, teeth, and other objects. Since the absorption spectra of objects such as teeth and food debris vary considerably from the absorption spectra of gingival tissue, the two can be distinguished. According to an embodiment, outliers are detected at points with absorption spectra that do not correspond to gingival tissue, essentially not showing the sharp spectral characteristics of hemoglobin absorption.

According to an embodiment, inflammation detection and localization module 420 determines a reflectance ratio of two or more different wavelengths. Using sample data of spectra obtained at 550 nm and 660 nm, for example, a ratio of reflectance would provide values of 2.38 for gingival tissue and 1.21 for teeth. Similarly, a ratio of reflectance between a blue wavelength (400 nm to 480 nm) and a green wavelength (480 nm to 550 nm) would provide values of 5.96 for gingival tissue and 1.44 for teeth. Therefore, the inflammation detection and localization module 420 could be configured or programmed with predetermined thresholds to identify gingival tissue. According to an embodiment, the system compares the reflectance ratio to the predetermined threshold and characterizes the location as being gingiva or non-gingiva based on whether the determined reflectance ratio exceeds or does not exceed the predetermined threshold. As just one example, a threshold of 2 in both of the above examples would decipher between gingiva and non-gingiva; reflectance ratios above 2 are characterized as gingiva, and reflectance ratios below 2 are characterized as non-gingiva. The system would then discard data from non-gingiva and would only continue to analyze data obtained from gingiva.

According to another embodiment, at step 550 of the method the system analyzes the obtained reflectance data to determine which of the plurality of analyzed locations are and/or are not gingiva by weighting the reflectance data. For example, the system may apply a high weight to reflectance data indicative of gingiva, and/or may apply a low weight to reflectance data indicative of anything other than gingiva. A system configured to weight reflectance data may only apply a weight to reflectance data indicative of gingiva, may only apply a weight to reflectance data indicative of non-gingiva, or may apply weights to both conditions during an analysis. The weighting process may be a programmed or predetermined weighting process, or may be a machine-learned weighting process. Using a weighting process, the system may utilize the one or more weighting factors to focus on reflectance data indicative of gingiva for further analysis, including an analysis of possible inflammation. In addition to removing non-gingiva reflectance data, and weighting gingiva and/or non-gingiva reflectance data, other methods of determining which of the plurality of analyzed locations are gingiva are possible.

At step 560 of the method, the controller 30 of oral care device 10 analyzes the demodulated reflectance data to determine which of the plurality of analyzed locations comprise inflamed gingiva. For example, the inflammation detection and localization module 420 analyzes the demodulated reflectance data for all locations, or only at locations determined to comprise gingiva. This analysis can be done while the device is obtaining data, or may be completed after the oral care device has finished with a session, or it may be performed on demand from the user.

According to an embodiment, the inflammation detection and localization module 420 determines or characterizes an approximate tissue oxygenation level of the gingival tissue using the reflectance data. Since tissue oxygen saturation is significantly decreased in gingivitis and periodontitis locations compared to healthy locations, the module may select a signal exhibiting the lowest tissue oxygenation, which identifies the highest level of gingival inflammation. This may be performed, for example, by selecting the maximum value from a given set of data, or by taking the average of the X-top percentile from a given set of data, among other methods. The module may obtain this information, for example, at each locale for which data was obtained. The inflammation detection and localization module 420 will thus generate information about locations within the mouth where there is likely to be gingival inflammation.

At step 570 of the method, the system or device optionally provides feedback to the user and/or a third-party regarding the inflammation localization information. The user interface 46 of the oral care device 10, for example, can provide direct and/or indirect feedback to the user while the oral care device is being used, or after a cleaning or scanning session. As an example, the device can provide direct feedback to the user after each measurement using audio, visual, haptic, and/or digital feedback whenever inflammation is detected.

According to another embodiment, the system or device may provide feedback to the user after a scanning session is complete. As an example, the system or device may provide feedback once a scanning session is complete by means of visual representation where the inflammation levels are displayed. The feedback may include, for example, a mouth map—using location sensing technology during measurement—either in their absolute form to show the inflammation levels or in relative forms to highlight one or more specific sites. According to an embodiment, the device can scale or otherwise rank inflammation levels using a variety of colors or other physical representations. For example, the user may only focus on areas of significant inflammation, or inflammation above a certain level.

According to an embodiment, the inflammation data is stored and/or communicated with a third party, either locally or remotely. For example, according to an embodiment, a patient may be instructed to use the oral care device during an appointment with a dental care professional, to assess inflammation. The inflammation information will then be communicated to the dental care professional, using a report or other mechanism. As another example, a user may collect inflammation data that is automatically or periodically transmitted to a remote healthcare professional or other intended or authorized entity where it can be analyzed continuously or during an appointment with the user.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for localizing gingival inflammation within a user's mouth using an oral care device, the method comprising:
    simultaneously emitting light by a plurality of light sources located in a light emitter of the oral care device, wherein the light emitter is positioned in a non-overlapping position relative to a light detector, wherein at least some of the plurality of light sources emit light of different wavelengths to result in a plurality of emitted light wavelengths, wherein each of the different wavelengths is modulated with a distinct code;
    obtaining, by the light detector of the oral care device, reflectance measurements from a location within the user's mouth to generate reflectance data for the location;
    demodulating, by a controller of the oral care device, the obtained reflectance data; and
    determining, by the controller using the demodulated reflectance data, whether gingiva at the location is inflamed.

2. The method of claim 1, further comprising a step of determining, by the controller using demodulated reflectance data, whether the location comprises gingiva.

3. The method of claim 1, further comprising a step of providing information regarding whether gingiva at a location comprises inflammation.

4. The method of claim 1, wherein the step of determining whether gingiva at a location is inflamed comprises determining an approximate tissue oxygenation level of the gingiva, wherein a low tissue oxygenation level indicates gingiva inflammation.

5. The method of claim 1, wherein the oral care device comprises a plurality of light detectors, each configured to obtain reflectance measurements from a different location within the user's mouth to generate reflectance data for that respective location.

6. The method of claim 5, wherein each of the plurality of light detectors obtain reflectance measurements simultaneously.

7. The method of claim 5, wherein the plurality of light detectors obtain reflectance measurements sequentially.

8. The method of claim 1, wherein the oral care device comprises a plurality of light emitters each comprising one or more light sources.

9. The method of claim 1, wherein the oral care device further comprises a user interface configured to provide information to the user before, during, or after a care session.

10. The method of claim 9, wherein the user interface is configured to provide feedback that includes information about where tissues are inflamed or how much inflammation is present.

11. A device configured to localize gingival inflammation within a user's mouth, comprising:
    a plurality of light sources located in a light emitter and simultaneously configured to emit light, wherein the light emitter is positioned in a non-overlapping position relative to a light detector, wherein at least some of the plurality of light sources emit light of different wavelengths to result in a plurality of emitted light wavelengths, wherein each of the different wavelengths is modulated with a distinct code;
    the light detector configured to obtain reflectance measurements from a location within the user's mouth to generate reflectance data for the location; and
    a controller configured to: (i) demodulate the obtained reflectance data; and (ii) determine, using the demodulated reflectance data, whether gingiva at the location is inflamed.

12. The device of claim 11, wherein the controller is further configured to determine, from the demodulated reflectance data, whether the location comprises gingiva.

13. The device of claim 11, wherein the device comprises a plurality of light detectors, each configured to obtain reflectance measurements from a different location within the user's mouth to generate reflectance data for that respective location.

14. The device of claim 13, wherein each of the plurality of light detectors obtain reflectance measurements simultaneously.

15. The device of claim 11, wherein the plurality of light sources and the light detector are positioned such that a surface at the location of the user's mouth is not directly illuminated by the plurality of light sources.

16. The device of claim 11, wherein the device is configured to report information relating to the gingival inflammation to the user or a third party.

17. The device of claim 11, wherein the device further comprises a sensor configured to provide information about the position of the device relative to the user's body part or a fixed point.

* * * * *